United States Patent [19]

Fischer

[11] Patent Number: 4,475,003

[45] Date of Patent: Oct. 2, 1984

[54] PREPARATION OF 1,1,1-TRICHLOROMETHYL COMPOUNDS

[75] Inventor: Martin Fischer, Ludwigshafen, Fed. Rep. of Germany

[73] Assignee: BASF Aktiengesellschaft, Ludwigshafen, Fed. Rep. of Germany

[21] Appl. No.: 417,659

[22] Filed: Sep. 13, 1982

[51] Int. Cl.$^3$ .................. C07C 31/36; C07C 31/34
[52] U.S. Cl. .................. 568/844; 568/848; 570/102; 570/117; 570/257; 570/261
[58] Field of Search .......... 568/844, 848; 570/102, 570/117, 257, 261; 585/942; 252/389.1, 389.6

[56] References Cited

U.S. PATENT DOCUMENTS

| 2,461,852 | 2/1949 | Stein et al. | 570/102 |
| 2,986,586 | 5/1961 | Graham et al. | 570/117 |
| 3,399,241 | 8/1968 | Smith | 568/848 |
| 3,449,262 | 6/1969 | Archer et al. | 570/117 |
| 4,053,380 | 10/1977 | Fujita et al. | 570/189 |

FOREIGN PATENT DOCUMENTS 39-26703 11/1964 Japan .................. 570/257

OTHER PUBLICATIONS

Kharasch, M. S. et al., *Science*, vol. 102, No. 2640, p. 128, (1945).
Kharasch, M. S. et al., *J. Amer. Chem. Soc.* 69, (1947), pp. 1100–1104.
Asscher et al., *J. Chem. Soc.* 1963, pp. 3921–3927.
Walling et al., *Organic Reactions* 13, (1963), p. 129.
D. Swern, Organic Peroxides, vol. I, Wiley, (1970), p. 275.
JACS, 73, (1951), pp. 880–881.
J. Am. Chem. Soc. 69, (1947), 1100–1104.
J. Chem. Soc. 1963, 3921–3927.
Org. Reactions 13 (1963), 129.

*Primary Examiner*—Natalie Trousof
*Assistant Examiner*—Bruce D. Gray
*Attorney, Agent, or Firm*—John H. Shurtleff

[57] ABSTRACT 1,1,1-Trichloromethyl compounds are prepared by a process in which chloroform is reacted with an olefin in the presence of a free-radical initiator and of a weakly basic alkali metal salt or alkaline earth metal salt, and are useful intermediates for the preparation of dyes, drugs and pesticides.

16 Claims, No Drawings

PREPARATION OF 1,1,1-TRICHLOROMETHYL COMPOUNDS

The present invention relates to a process for the preparation of 1,1,1-trichloromethyl compounds by reacting chloroform with an olefin in the presence of a free-radical initiator and of a weakly basic alkali metal salt or alkaline earth metal salt.

It has been disclosed that, when chloroform is reacted with oct-1-ene in the presence of benzoyl peroxide, 1,1,1-trichlorononane is formed in a yield of from 22 to 40%, based on the olefin, and with a selectivity of from 41 to 48%, conversion of the olefin being incomplete (J. Amer. Chem. Soc. 69 (1947), 1100–1104, in particular page 1104; and J. Chem. Soc. 1963, 3921–3927, in particular page 3927). The free-radical addition reactions of chloroform with other olefins also in general give only moderate yields (C. Walling and E. S. Hugser, Org. Reactions 13 (1963), 129).

In order to suppress the olefin polymerization which competes with the free-radical addition of chloroform at the C—C double bonds, it is advantageous to use a very large excess of chloroform. In German Laid-Open Application DOS No. 2,616,528, Example 1, the yield of 1,1,1-trichloro-4-methyl-pentan-4-ol is said to be 69% when the starting materials, ie. chloroform and dimethylvinylcarbonyl, are employed in the molar ratio of 9.4:1. However, in order to obtain good space/time yields and keep working-up costs low, the chloroform should be present in only a very small excess. The free radical addition reaction of chloroform with an olefin cannot be carried out in a reaction vessel containing iron, since the reaction releases traces of hydrogen chloride which attacks the vessel. Moreover, traces of iron ions in the reaction mixture lead to undesirable side-reactions, for example to HCL being split off to an increasing extent from the products, to transfer of chlorine atoms, and to water being split off when an OH-containing starting material II is used. Although these complications can be avoided by carrying out the reaction in a reactor lined with glass or enamel, pressure-resistant reactors of this type are substantially more expensive than those made of steel.

I have found that 1,1,1-trichloromethyl compounds of the formula

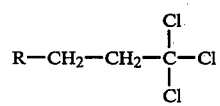

where R is an aliphatic radical, are advantageously obtained by reacting chloroform with an olefin of the formula

where R has the above meaning, in the presence of a free-radical initiator, if the reaction is carried out in the presence of a weakly basic alkali metal salt or alkaline earth metal salt.

Where 3-methylbut-1-en-3-ol is used, the reaction may be represented by the following equation:

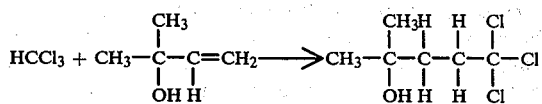

Compared with the conventional processes, the process according to the invention gives 1,1,1-trichloromethyl compounds in better yields and by a simpler and more economical route. Thus, for example, the yield of 1,1,1-trichlorononane increases from 59% to 72% when 8% by weight, based on the olefin, of anhydrous sodium acetate is added to the reaction mixture comprising chloroform, oct-1-ene and tert.-butyl perbenzoate. As a result of the addition, in accordance with the invention, of a weakly basic alkali metal salt or alkaline earth metal salt, the chloroform addition reaction may be carried out in a steel vessel, without iron being dissolved out from the wall material.

The starting materials are employed in stoichiometric amounts or in excess of either reactant with reference to the other reactant, advantageously in a ratio of from 2 to 10, in particular from 4 to 8, moles of chloroform per mole of starting material II. No solvent is required. Preferred starting materials II, and accordingly preferred end products I, are those of the formulae where R is alkyl of 1 to 20, in particular of 1 to 8, carbon atoms, which can be unsubstituted or substituted by OH groups and/or chlorine atoms, preferably by 1 or 2 OH groups and/or chlorine atoms.

Examples of suitable starting materials II are therefore prop-1-ene, but-1-ene, isobutylene, pent-1-ene, hex-1-ene, hept-1-ene, oct-1-ene, non-1-ene, dec-1-ene, dodec-1-ene, prop-2-en-1-ol, 3-methylbut-1-ene, 3-methylbut-1-en-3-ol, 3-chloroprop-1-ene, 3-chlorobut-1-ene, 3,4-dichlorobut-1-ene, but-1-en-3-ol and but-1-ene-3,4-diol.

For the purposes of the invention, weakly basic salts are all those which are capable of accepting hydrogen chloride to form salts. Alkali metal salts or alkaline earth metal salts of acids with dissociation constants $\leq 10^{-3}$ are advantageously employed.

Examples of suitable weakly basic salts are the alkali metal salts or alkaline earth metal salts of organic acids, such as formic acid, acetic acid, propionic acid, butyric acid, malonic acid, succinic acid, maleic acid and benzoic acid, as well as the basic salts of polybasic mineral acids, such as phosphoric acid, boric acid, phosphorous acid, sulfurous acid or silicic acid. Alkali metal and alkaline earth metal carbonates and bicarbonates are also suitable. Preferred salts are those of magnesium, calcium, lithium and in particular sodium and potassium.

The weakly basic salts are employed in amounts of from 1 to 20, preferably 3 to 12, % by weight, based on starting material II.

For the purposes of the invention, free radical initiators are initiators or catalysts which initiate or accelerate polymerization. As regards their definition, reference may be made to Houben-Weyl, Methoden der Org. Chemie, Volume 14/1, page 56.

Initiators which are conventionally used to start free radical chain reactions may be used as free-radical initiators for the chloroform addition reaction. These include dialkyl peroxides, eg. di-tert.-butyl peroxide or 2,5-dimethyl-2,5-bis-(tert.-butylperoxy)-hexane, peresters, eg. tert.-butyl peroxypivalate, tert.-butyl peroxyoctoate, tert.-butyl peroxyisobutyrate, tert.-butyl peroxymaleate, 2,5-dimethylhexane 2,5-diperbenzoate, tert.-butyl peracetate, di-tert.-butyl diperphthalate or tert.-butyl perbenzoate, diacyl peroxides, eg. pelargonyl peroxide, decanoyl peroxide, lauroyl peroxide, propionyl peroxide, acetyl peroxide, benzoyl peroxide or p-chlorobenzoyl peroxide, hydroperoxides, eg. tert.-butyl hydroperoxide, cumene hydroperoxide or ketone hydroperoxides, and peroxydicarbonates, eg. bis-(4-tert.-butylcyclohexyl) peroxydicarbonate, dicyclohexyl peroxydicarbonate, bis-(2-ethylhexyl) peroxydicarbonate, dibutyl peroxydicarbonate and diisopropyl peroxydicarbonate.

The amount of free radical initiator required for the addition reaction of chloroform with the unsaturated starting material II depends on the structure of the starting material II, the temperature and the structure of the initiator employed. Advantageously from 1 to 10, preferably from 3 to 7, mole %, based on starting material II, of the peroxide are used.

The reaction is carried out in general at from 60 to 180° C., preferably from 110° to 150° C., under atmospheric or superatmospheric pressure, either continuously or batchwise. The reaction time depends on the half-life of the free-radical initiator employed. To achieve good utilization of the initiator, the reaction time is advantageously fixed at from 3 to 6 times the half-life of the peroxide at the preselected temperature. However, longer reaction times have no adverse effect when the starting materials II are thermally stable. Advantageously, the temperature and the initiator are chosen so that the reaction time can be set at from 0.5 to 24 hours, preferably from 2 to 8 hours.

The reaction may be carried out as follows: a mixture of chloroform, the weakly basic salt, starting material II and the free radical initiator is kept at the reaction temperature for the above reaction time. The end product is then isolated in a conventional manner, for example by adding water and fractionally distilling the organic phase.

Since free radical chloroform addition reactions are highly exothermic, it is advantageous for safety reasons, when the reactions are carried out on an industrial scale, to meter the starting material II a little at a time into the reaction vessel. To provide a uniform supply of free radicals for initiation purposes over the entire reaction time, it is advantageous also to meter in the free radical initiator. The metering times of starting material II and free radical initiator are advantageously from ⅓ to ⅔ of the total reaction time. After the reaction is complete, the basic salt can be filtered off, or dissolved in water and separated off with the aqueous phase. The chloroform which has not been consumed during the reaction is distilled off. The end product I remaining in the residue can be isolated by crystallization or preferably by distillation under reduced pressure.

The 1,1,1-trichloromethyl compounds obtainable by the novel process are useful intermediates for the preparation of dyes, drugs and pesticides. They are starting materials for the preparation of the corresponding carboxylic acids, which are obtained by hydrolysis of the trichloromethyl group. 1,1,1-Trichloro-4-methylpentan-4-ol is an intermediate for the preparation of the pyrethroids permethrin and cypermethrin (German Laid-Open Application DOS No. 2,616,528, and Nachr. Chem. Tech. Lab. 26 (1978), 120–128). As regards the use of these compounds, reference may be made to the above publications.

In the Examples which follow, parts are by weight and bear the same relation to parts by volume as that of the kilogram to the liter. The purity of the end product I was determined by means of gas chromatography.

COMPARATIVE EXAMPLE 1

In an enamel kettle, 6,500 parts by volume of chloroform are heated to 130° C., with stirring, resulting in a pressure of 6 bar. A mixture of 1,190 parts of oct-1-ene and 120 parts of tert.-butyl perbenzoate is pumped in over 5 hours, and the mixture is then kept at 130° C. for a further 4 hours. The mixture is cooled, after which the excess chloroform is distilled over under atmospheric pressure, and the residue is distilled under reduced pressure. 1,757 parts of distillate containing 83% by weight of 1,1,1-trichlorononane pass over at 78°–86° C./0.4 mbar. Yield: 58.3% of theory.

COMPARATIVE EXAMPLE 2

In an enamel kettle, 6,500 parts by volume of chloroform are heated to 120° C., with stirring. A solution of 120 parts of dibenzoyl peroxide in 1,190 parts of 3-methylbut-1-en-3-ol and 500 parts by volume of chloroform is pumped in over 6.5 hours, and the mixture is then kept at 120° C. for a further 4 hours. The mixture is cooled, after which the excess chloroform is distilled off under atmospheric pressure, and the residue is distilled under reduced pressure. 1,681 parts of distillate containing 79% by weight of 1,1,1-trichloro-4-methylpentan-4-ol of melting point 39°–40° C. pass over at 64°–68° C./0.4 mbar. Yield: 46.7% of theory.

COMPARATIVE EXAMPLE 3

86 parts of 3-methylbut-1-en-3-ol, 8.6 parts of di-tert.-butyl peroxide and 750 parts by volume of chloroform are heated at 130° C. for 6 hours in a stirred autoclave lined with Hastelloy C. The mixture is cooled, after which the excess chloroform is distilled over under atmospheric pressure, and the end product at 64°–68° C./0.4 mbar. 152.1 parts of a solid product containing 77% by weight of 1,1,1-trichloro-4-methylpentan-4-ol are obtained. Yield: 57% of theory.

COMPARATIVE EXAMPLE 4

In a V2A stainless steel stirred kettle, 9,000 parts by volume of chloroform are heated to 150° C., with stirring. A solution of 103 parts of di-tert.-butyl peroxide in 1,032 parts of 3-methylbut-1-en-3-ol is pumped in over one hour, and the mixture is heated at 150° C. for a further 10 hours. It is then worked up by a procedure similar to that described in Comparative Example 2, and 1,163 parts of a distillate which does not crystallize and which contains 60% by weight of 1,1,1-trichloro-4-methylpentan-4-ol are obtained. Yield: 28.3% of theory.

EXAMPLE 1

In an enamel kettle, 6,500 parts by volume of chloroform and 100 parts of anhydrous sodium acetate are heated to 130° C., with stirring. A mixture of 1,190 parts of oct-1-ene and 120 parts of tert.-butyl perbenzoate is pumped in over 5 hours, and the mixture is then kept at 130° C. for a further 4 hours. The mixture is cooled, after which 2,000 parts by volume of water are added, the aqueous phase is separated off, and the excess chloroform is distilled off. The residue is then distilled under reduced pressure, and 2,081 parts of distillate which contain 85% by weight of 1,1,1-trichlorononane are obtained at 78°–86° C./0.4 mbar. Yield: 72% of theory.

EXAMPLE 2

In an enamel kettle, 6,500 parts by volume of chloroform and 100 parts of sodium acetate are heated to 120° C., with stirring. A mixture of 1,190 parts of 3-methylbut-1-en-3-ol, 120 parts of dibenzoyl peroxide and 500 parts by volume of chloroform is pumped in over 5.5 hours, and the mixture is then kept at 120° C. for a further 4 hours. The mixture is cooled, after which 2,000 parts by volume of water are added, the aqueous phase is separated off, and the excess chloroform is distilled off. The solid residue is then distilled under reduced pressure, and 2,384 parts of distillate which contain 78% by weight of 1,1,1-trichloro-4-methylpentan-4-ol of melting point 39° C. are obtained at 64°–68° C./0.4 mbar. Yield: 65.4% of theory.

EXAMPLE 3

In an enamel kettle, 6,500 parts by volume of chloroform and 100 parts of anhydrous sodium phosphate are heated to 120° C., with stirring. A mixture of 1,190 parts of 3-methylbut-1-en-3-ol and 120 parts of tert.-butyl perbenzoate is pumped in over 4 hours, and the mixture is then kept at 120° C. for a further 4 hours. It is then worked up by a procedure similar to that described in Example 2, and 2,235 parts of distillate containing 79% by weight of 1,1,1-trichloro-4-methylpentan-4-ol are obtained. Yield: 62.1% of theory.

EXAMPLE 4

In an enamel kettle, 6,500 parts by volume of chloroform and 100 parts of sodium acetate are heated to 120° C., with stirring. A mixture of 1,190 parts of 3-methylbut-1-en-3-ol and 120 parts of tert.-butyl perbenzoate is pumped in over 4 hours, and the mixture is then kept at 120° C. for a further 4 hours. It is then worked up by a procedure similar to that described in Example 2, and 2,395 parts of distillate containing 80% by weight of 1,1,1-trichloro-4-methylpentan-4-ol are obtained. Yield: 67.4% of theory.

EXAMPLE 5

The reaction in Example 4 is repeated using 80 parts of tert.-butyl perbenzoate instead of 120 parts. 2,245 parts of distillate containing 78% by weight of 1,1,1-trichloro-4-methylpentan-4-ol are obtained. Yield: 61.6% of theory.

EXAMPLE 6

In an enamel kettle, 6,500 parts by volume of chloroform and 100 parts of sodium acetate are heated to 120° C., with stirring. A mixture of 1,190 parts of 3-methylbut-1-en-3-ol and 120 parts of tert.-butyl perbenzoate is pumped in over 4 hours, and the mixture is then kept at 120° C. for a further 8 hours. It is then worked up by a procedure similar to that described in Example 2, and 2,422 parts of distillate containing 81% by weight of 1,1,1-trichloro-4-methylpentan-4-ol are obtained. Yield: 69% of theory.

EXAMPLE 7

The reaction in Example 6 is repeated, except that the olefin and the peroxide are pumped in over 6 hours and the mixture is then stirred for a further 12 hours at 120° C. 2,524 parts of distillate containing 80% by weight of 1,1,1-trichloro-4-methylpentan-4-ol are obtained. Yield: 71% of theory.

EXAMPLE 8

In an enamel kettle, 6,500 parts by volume of chloroform and 100 parts of sodium acetate are heated to 130° C., with stirring. A mixture of 1,190 parts of 3-methylbut-1-en-3-ol and 120 parts of di-tert.-butyl peroxide is pumped in over 4 hours, and the mixture is then kept at 130° C. for a further 7 hours. It is then worked up by a procedure similar to that described in Example 2, and 2,614 parts of distillate containing 78% by weight of 1,1,1-trichloro-4-methylpentan-4-ol are obtained. Yield: 71.6% of theory.

EXAMPLE 9

86 parts of 3-methylbut-1-en-3-ol, 8.6 parts of di-tert.-butyl peroxide, 16.8 parts of sodium bicarbonate and 750 parts by volume of chloroform are heated at 130° C. for 6 hours in a stirred autoclave lined with Hastelloy C. The mixture is worked up by a procedure similar to that described in Example 2, and 190 parts of distillate containing 77% by weight of 1,1,1-trichloro-4-methylpentan-4-ol are obtained. Yield: 71.2% of theory.

EXAMPLE 10

The reaction in Comparative Example 4 is repeated, with the addition of 87 parts of sodium acetate. 2,133 parts of a distillate which crystallizes and contains 74% by weight of 1,1,1-trichloro-4-methylpentan-4-ol are obtained. Yield: 64% of theory.

I claim:

1. A process for the preparation of a 1,1,1-trichloromethyl compound of the formula

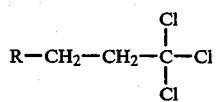
    I where R is an aliphatic radical by reacting chloroform with an olefin of the formula

    II where R has the above meaning, in the presence of a free-radical initiator wherein the reaction is carried out in the presence of a weakly basic alkali metal salt or alkaline earth metal salt in an amount of from 1 to 20% by weight, based on starting material II.

2. A process as claimed in claim 1, wherein the reaction is carried out using from 2 to 10 moles of chloroform per mole of starting material II.

3. A process as claimed in claim 1, wherein the reaction is carried out using, as the weakly basic salt, an alkali metal salt or alkaline earth metal salt of formic acid, acetic acid, propionic acid, butyric acid, malonic acid, succinic acid, maleic acid or benzoic acid.

4. A process as claimed in claim 1, wherein the reaction is carried out using, as the weakly basic salt, a basic salt of phosphoric acid, boric acid, phosphorous acid, sulfurous acid or silicic acid.

5. A process as claimed in claim 1, wherein the reaction is carried out using a weakly basic salt in an amount of from 3 to 12% by weight, based on starting material II.

6. A process as claimed in claim 1, wherein the reaction is carried out using, and the free-radical initiator, a di-tert.-butyl peroxide, 2,5-dimethyl-2,5-bis-(tert.-butylperoxy)-hexane, tert.-butyl peroxypivalate, tert.-butyl peroxyoctoate, tert.-butyl peroxyisobutyrate, tert.-butyl peroxymaleate; 2,5-dimethylhexane 2,5-diperbenzoate, tert.-butyl peracetate, di-tert.-butyl diperphthalate, tert.-butyl perbenzoate, pelargonyl peroxide, decanoyl peroxide, lauroyl peroxide, propionyl peroxide, acetyl peroxide, benzoyl peroxide, p-chlorobenzoyl peroxide, tert.-butyl hydroperoxide, cumene hydroperoxide, ketone hydroperoxide, bis-(4-tert.-butylcyclohexyl) peroxydicarbonate, dicyclohexyl peroxydicarbonate, bis-(2-ethylhexyl) peroxydicarbonate, dibutyl peroxydicarbonate or diisopropyl peroxydicarbonate.

7. A process as claimed in claim 1, wherein the reaction is carried out using from 1 to 10 moles of peroxide per mole of starting material II.

8. A process as claimed in claim 1, wherein the reaction is carried out at from 60° to 180° C.

9. A process as claimed in claim 1, wherein the reaction is carried out at from 110° to 150° C.

10. A process as claimed in claim 1, wherein the reaction is carried out for from 0.5 to 24 hours.

11. A process as claimed in claim 1 wherein the weakly basic salt is sodium acetate.

12. A process as claimed in claim 1 wherein the weakly basic salt is sodium phosphate.

13. A process as claimed in claim 1 wherein the weakly basic salt is sodium bicarbonate.

14. A process as claimed in claim 1 wherein the free-radical initiator is tert.-butyl perbenzoate.

15. A process as claimed in claim 1 wherein the free-radical initiator is dibenzoyl peroxide.

16. A process as claimed in claim 1 wherein the free-radical initiator is di-tert.-butyl peroxide.

* * * * *